US012678774B2

(12) United States Patent
Hwang et al.

(10) Patent No.: US 12,678,774 B2
(45) Date of Patent: Jul. 14, 2026

(54) CATALYST FOR HYDROGENATION REACTION AND MANUFACTURING METHOD THEREFOR

(71) Applicants: LG CHEM, LTD., Seoul (KR); KOREA ADVANCED INSTITUTE OF SCIENCE AND TECHNOLOGY, Daejeon (KR)

(72) Inventors: Sunhwan Hwang, Daejeon (KR); Dong Hyun Ko, Daejeon (KR); Kyong Yong Cha, Daejeon (KR); Young Hwan Park, Daejeon (KR); Minkee Choi, Daejeon (KR)

(73) Assignees: LG Chem, Ltd., Seoul (KR); Korea Advanced Institute of Science and Technology, Daejeon (KR)

( * ) Notice: Subject to any disclaimer, the term of this patent is extended or adjusted under 35 U.S.C. 154(b) by 668 days.

(21) Appl. No.: 18/027,578

(22) PCT Filed: Jun. 24, 2022

(86) PCT No.: PCT/KR2022/009004
§ 371 (c)(1),
(2) Date: Mar. 21, 2023

(87) PCT Pub. No.: WO2023/003190
PCT Pub. Date: Jan. 26, 2023

(65) Prior Publication Data

US 2023/0372906 A1 Nov. 23, 2023

(30) Foreign Application Priority Data

Jul. 19, 2021 (KR) ........................ 10-2021-0094099

(51) Int. Cl.
*B01J 23/44* (2006.01)
*B01J 21/04* (2006.01)
(Continued)

(52) U.S. Cl.
CPC ............... *B01J 23/44* (2013.01); *B01J 21/04* (2013.01); *B01J 31/06* (2013.01); *B01J 35/60* (2024.01);
(Continued)

(58) Field of Classification Search
CPC ... B01J 23/44; B01J 21/04; B01J 31/06; B01J 35/60; B01J 37/0201; B01J 2235/30;
(Continued)

(56) References Cited

U.S. PATENT DOCUMENTS

2013/0303813 A1 11/2013 Cabiac et al.
2015/0231612 A1 8/2015 Dai et al.
(Continued)

FOREIGN PATENT DOCUMENTS

CN 102127226 A 7/2011
CN 105085917 A 11/2015
(Continued)

OTHER PUBLICATIONS

English machine translation of CN110639613A (Year: 2020).*
(Continued)

*Primary Examiner* — Anthony J Zimmer
*Assistant Examiner* — Abdul-Rahman Yusuf Waleed Smari
(74) *Attorney, Agent, or Firm* — Bryan Cave Leighton Paisner LLP

(57) ABSTRACT

The catalyst for a hydrogenation reaction according to an exemplary embodiment of the present application comprises: a porous carrier; a catalytic component supported on the porous carrier; and a polymer provided on at least a part of the surfaces of the porous carrier and the catalytic component and comprising the repeating unit represented by Chemical Formula 1.

8 Claims, 5 Drawing Sheets

(51) Int. Cl.

| | |
|---|---|
| ***B01J 31/06*** | (2006.01) |
| ***B01J 35/60*** | (2024.01) |
| ***B01J 37/02*** | (2006.01) |
| ***C07C 5/09*** | (2006.01) |

(52) U.S. Cl.
CPC ............. *B01J 37/0201* (2013.01); *C07C 5/09* (2013.01); *B01J 2235/30* (2024.01); *C07C 2521/04* (2013.01); *C07C 2523/44* (2013.01); *C07C 2531/06* (2013.01)

(58) Field of Classification Search
CPC ........ B01J 23/40; B01J 23/70; B01J 31/0218; B01J 2231/645; B01J 37/02; C07C 5/09; C07C 2521/04; C07C 2523/44; C07C 2531/06; Y02P 20/52
See application file for complete search history.

(56) References Cited

U.S. PATENT DOCUMENTS

| | | | |
|---|---|---|---|
| 2022/0105501 | A1 | 4/2022 | Suh et al. |
| 2022/0118432 | A1 | 4/2022 | Suh et al. |
| 2022/0134323 | A1 | 5/2022 | Suh et al. |

FOREIGN PATENT DOCUMENTS

| | | | |
|---|---|---|---|
| CN | 106861715 | A | 6/2017 |
| CN | 110639613 | A | 1/2020 |
| JP | 2013-248612 | A | 12/2013 |
| KR | 10-2015-0041033 | A | 4/2015 |
| KR | 10-2021-0038296 | A | 4/2021 |
| KR | 10-2021-0038297 | A | 4/2021 |
| KR | 10-2021-0038298 | A | 4/2021 |

OTHER PUBLICATIONS

Hyun et al., "Tailoring a Dynamic Metal-Polymer Interaction to Improve Catalyst Selectivity and Longevity in Hydrogenation" Angew . Chem. Int. Ed. 60, Mar. 2021, 12482-12489 (Year: 2021).*

Huang et al., "Polyphenylene sulfide as an efficient solid-phase ligand for improved selective alkyne hydrogenation" Molecular Catalysis 519, Jan. 1-11, 2022, (Year: 2022).*

Office Action of Korea Patent Office in Application No. 10-2022-0077317, dated Dec. 16, 2024.

Lee et al., "Dynamic metal-polymer interaction for the design of chemoselective and long-lived hydrogenation catalysts", Science Advances 2020; 6, Jul. 8, 2020.

Yun, et al. "Cross-Linked "Poisonous" Polymer: Thermochemically Stable Catalyst Support for Tuning Chemoselectivity", 2016, ACS Catalysis, vol. 6, pp. 2435-2442.

Park, et al., "Breaking the Inverse Relationship Between Catalytic Activity and Selectivity in Acetylene Partial Hydrogenation Using Dynamic Metal-Polymer Interaction" Journal of Catalysis, 2021, vol. 404, pp. 716-725.

* cited by examiner

[Figure 1]
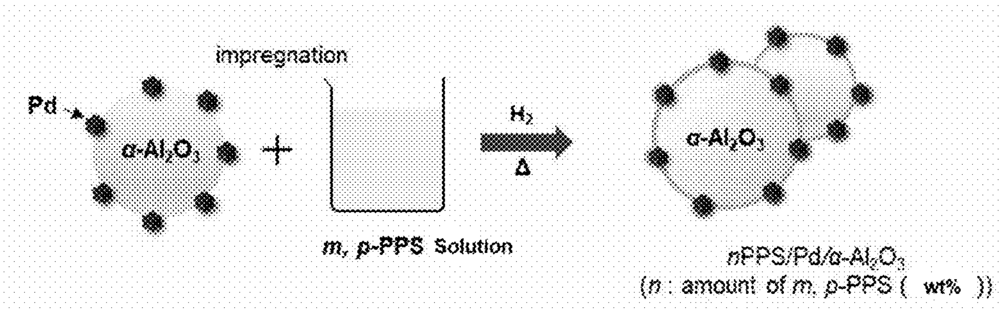
[Figure 2]
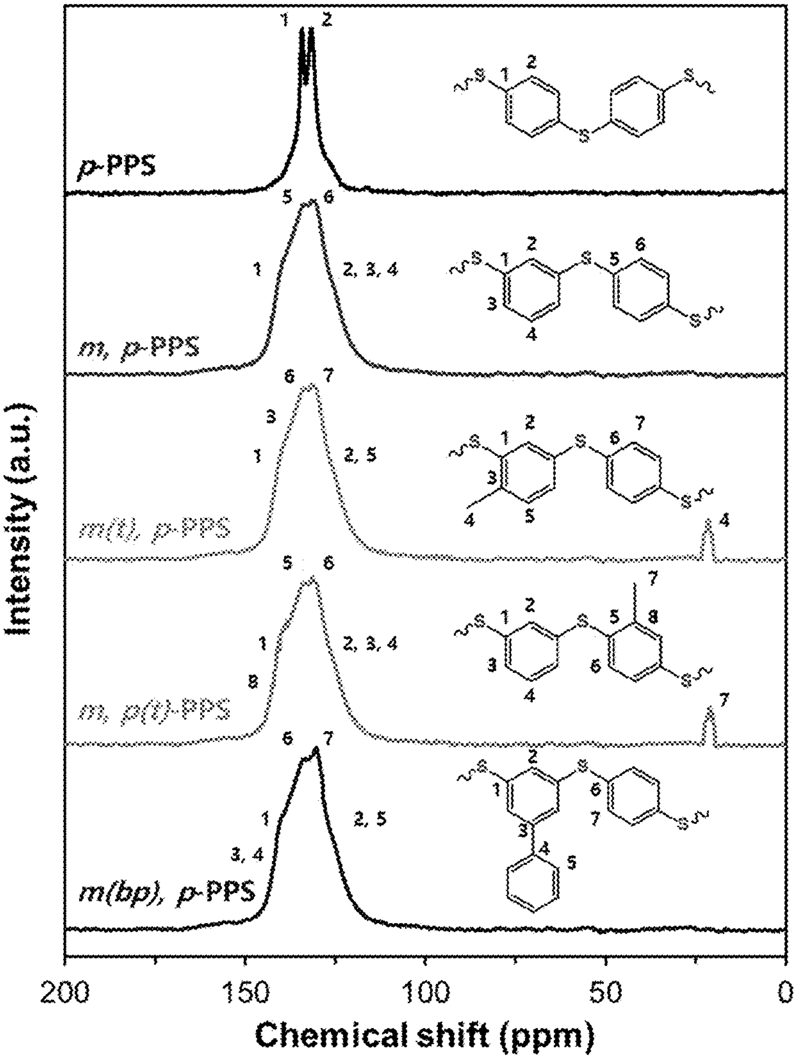

[Figure 3]
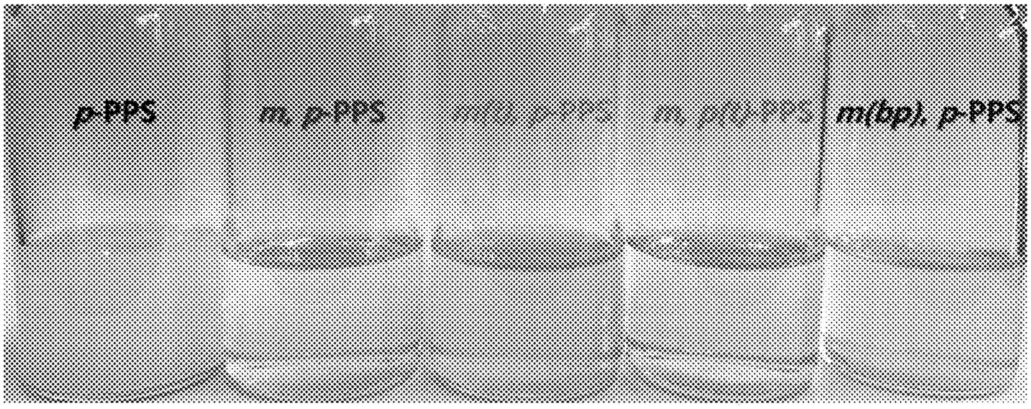
[Figure 4]
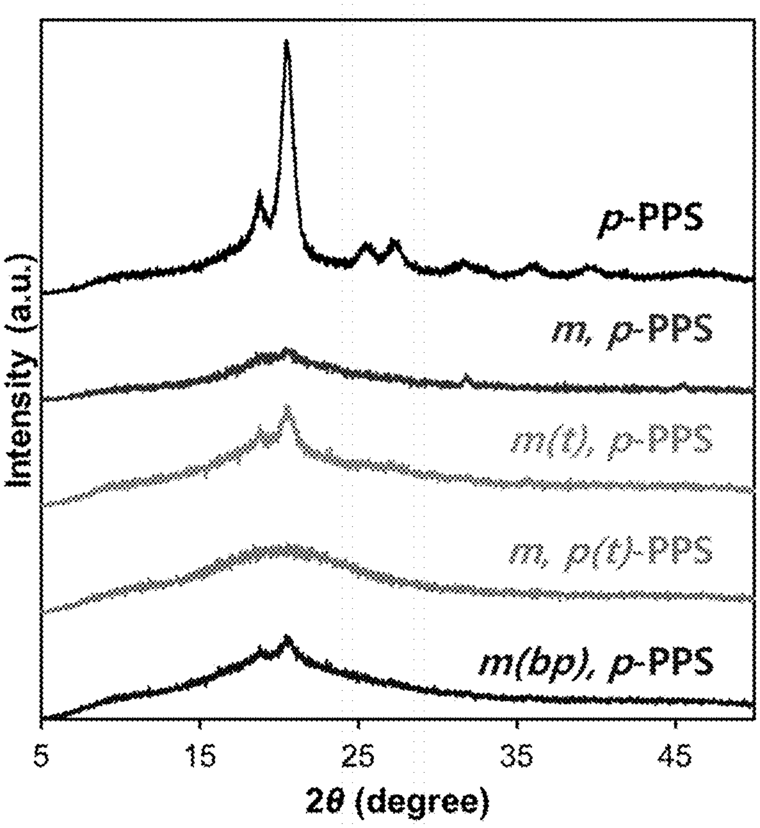

[Figure 5]
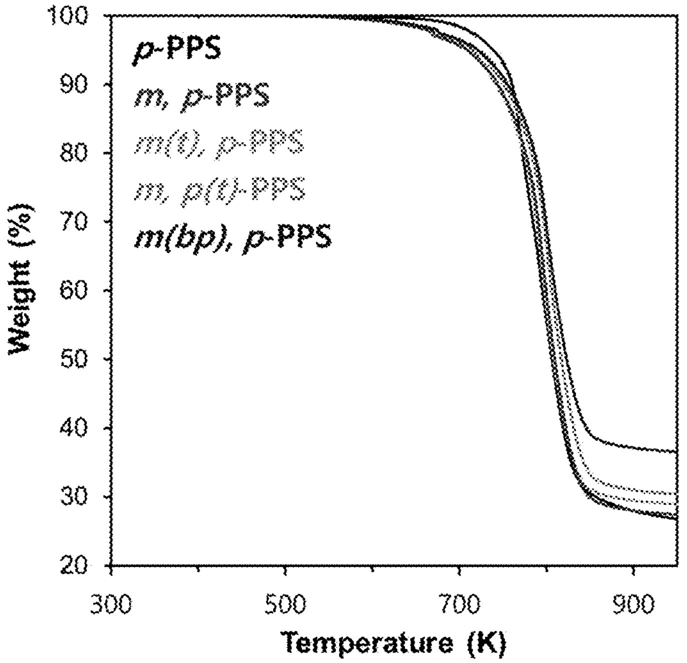
[Figure 6]
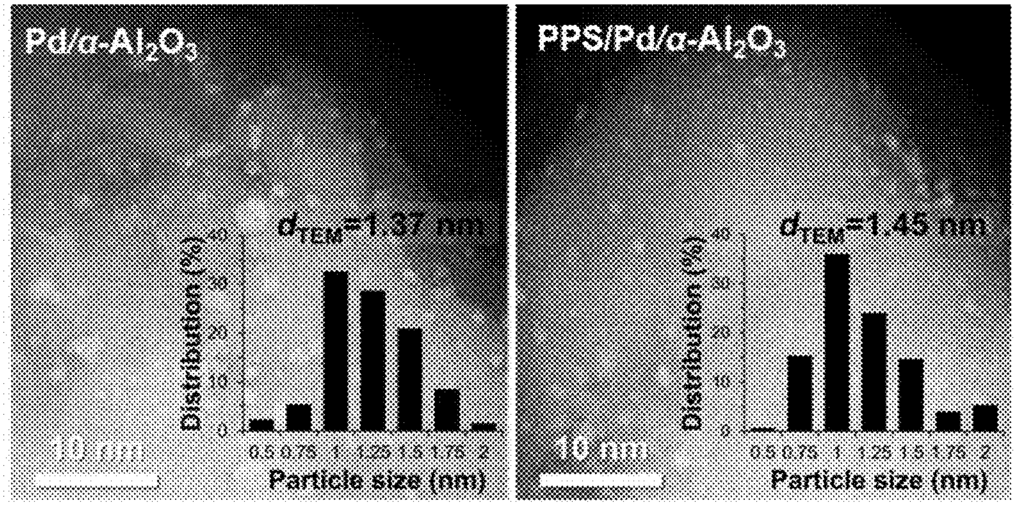

[Figure 7]
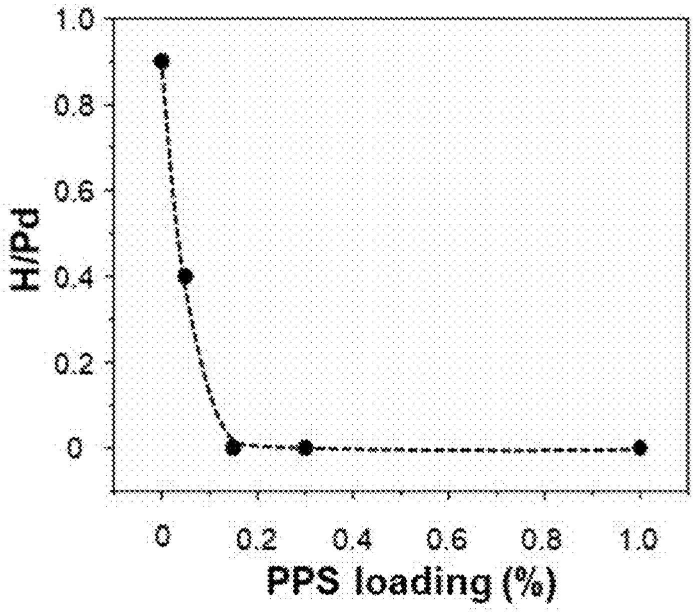
[Figure 8]
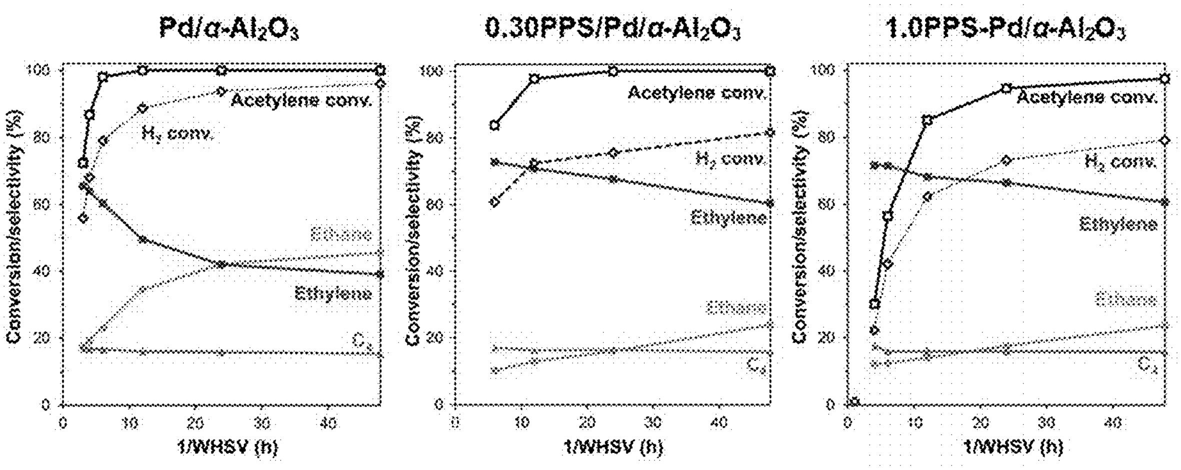

[Figure 9]
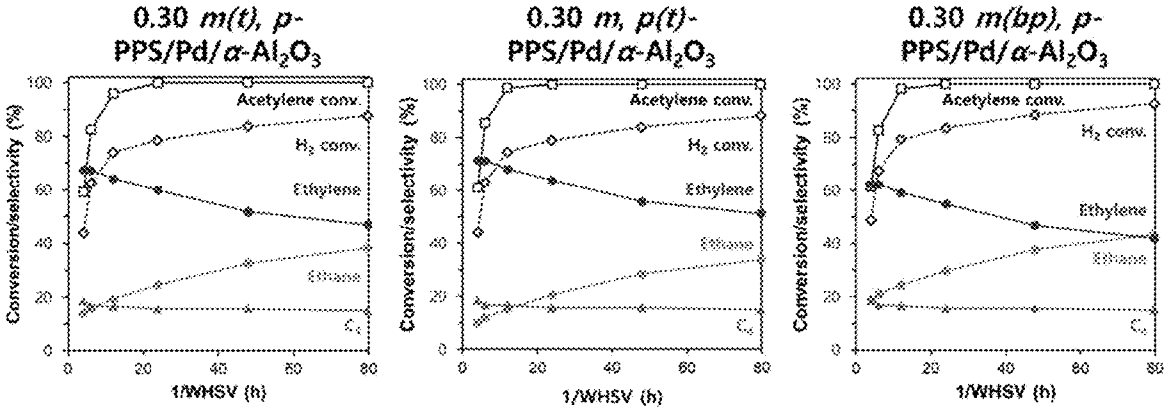
[Figure 10]
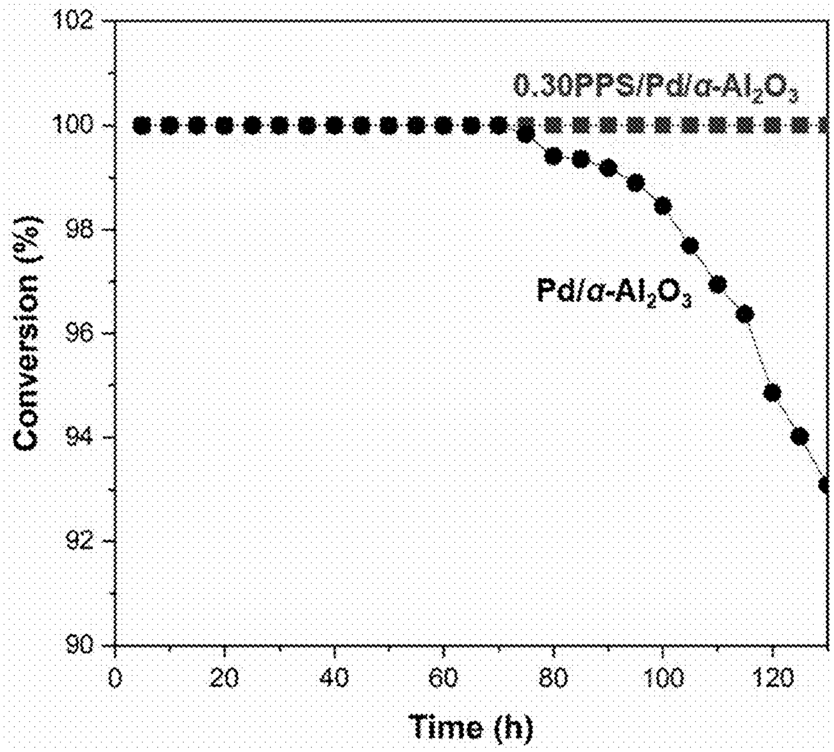

CATALYST FOR HYDROGENATION REACTION AND MANUFACTURING METHOD THEREFOR

CROSS-REFERENCE TO RELATED APPLICATIONS

This application is a National Phase entry pursuant to 35 U.S.C. § 371 of International Application No. PCT/KR2022/009004, filed on Jun. 24, 2022, and claims the benefit of and priority to Korean Patent Application No. 10-2021-0094099, filed on Jul. 19, 2021, the disclosures of which are incorporated by reference in their entirety for all purposes as if fully set forth herein.

TECHNICAL FIELD

The present disclosure relates to a catalyst for a hydrogenation reaction and a method for producing the same.

BACKGROUND

Oil refinery and petrochemical plants produce large amounts of hydrocarbons, which contain large amounts of unsaturated hydrocarbons which cause problems during subsequent process steps or storage periods. Examples of these unsaturated hydrocarbons comprise acetylene, propyne, propadiene, butadiene, vinylacetylene, butyne, phenylacetylene, styrene and the like.

As an example, acetylene is known to reduce the activity of a catalyst in an ethylene polymerization process and cause a deterioration in the quality of a polymer. Therefore, in a process of synthesizing polyethylene from ethylene, the concentration of acetylene contained in ethylene raw materials needs to be reduced to the minimal level.

These undesired unsaturated compounds are usually removed to several PPM or less by a selective hydrogenation reaction. It is very important to enhance the selectivity from a reaction of selectively hydrogenating unsaturated compounds to the desired compound and avoid coke formation, which reduces the reaction activity.

In the related art, nickel sulfate, tungsten/nickel sulfate or copper containing catalysts have been used for selective hydrogenation reactions. However, these catalysts have low catalytic activity even at high temperatures, and thus reduce polymer formation. Further, supported palladium (Pd) or Pd and silver (Ag) containing catalysts based on alumina or silica are also used in the selective hydrogenation process, but the selectivity is unsatisfactory or the activity is low.

Therefore, there is a need in the art for developing a catalyst for a hydrogenation reaction, which has excellent selectivity for a product of hydrogenation reaction and excellent catalytic activity.

The background description provided herein is for the purpose of generally presenting context of the disclosure. Unless otherwise indicated herein, the materials described in this section are not prior art to the claims in this application and are not admitted to be prior art, or suggestions of the prior art, by inclusion in this section.

DETAILED DESCRIPTION OF THE INVENTION

Technical Problem

The present application provides a catalyst for a hydrogenation reaction and a method for producing the same.

Technical Solution

An exemplary embodiment of the present application provides a catalyst for a hydrogenation reaction, comprising:

a porous carrier;

a catalytic component supported on the porous carrier; and a polymer provided on at least a part of the surfaces of the porous carrier and the catalytic component and comprising a repeating unit represented by the following Chemical Formula 1.

[Chemical Formula 1]

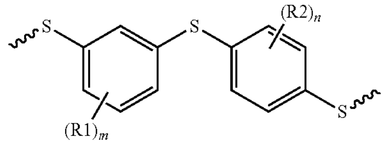

In Chemical Formula 1,

R1 and R2 are the same as or different from each other, and are each independently hydrogen, an alkyl group having 1 to 10 carbon atoms, or an aryl group having 6 to 20 carbon atoms, or adjacent groups of R1 or R2 may be bonded to each other to form a hydrocarbon ring, and m and n are each independently an integer from 0 to 4.

Further, another exemplary embodiment of the present application provides a method for producing a catalyst for a hydrogenation reaction, the method comprising:

supporting a catalytic component on a porous carrier; and supporting a polymer comprising the repeating unit represented by Chemical Formula 1 on the porous carrier on which the catalytic component is supported.

Advantageous Effects

According to an exemplary embodiment of the present application, the selectivity for a product in a hydrogenation reaction can be improved by additionally supporting a polymer comprising the repeating unit represented by Chemical Formula 1 on a catalyst for a hydrogenation reaction in which a catalytic component is supported on a porous carrier.

Further, the catalyst for a hydrogenation reaction according to an exemplary embodiment of the present application has excellent long-term stability, and thus is characterized by being capable of improving the catalyst service life.

BRIEF DESCRIPTION OF DRAWINGS

FIG. 1 is a view schematically illustrating a method for producing a catalyst for a hydrogenation reaction as an exemplary embodiment of the present application.

FIG. 2 is a view illustrating cross polarization magic-angle spinning $^{13}C$ nuclear magnetic resonance (CP/MAS $^{13}C$ NMR) analysis results of the polymers according to Synthesis Examples 1 to 4 as an exemplary embodiment of the present application.

FIG. 3 is a view illustrating the results of evaluating the solubility characteristics of the polymers according to Synthesis Examples 1 to 4 as an exemplary embodiment of the present application.

FIG. 4 is a view illustrating the crystallinity of the polymers according to Synthesis Examples 1 to 4 as an exemplary embodiment of the present application.

FIG. 5 is a view illustrating thermal stability according to Synthesis Examples 1 to 4 as an exemplary embodiment of the present application.

FIG. 6 is a view illustrating the transmission electron microscope (TEM) images of the catalysts according to Example 1 and Comparative Example 1 as an exemplary embodiment of the present application.

FIG. 7 is a view illustrating the hydrogen chemisorption results of the catalyst according to Example 1 as an exemplary embodiment of the present application.

FIG. 8 is a set of views illustrating the selectivity for ethylene according to the conversion of acetylene during a hydrogenation reaction using the catalysts according to Examples 1 and 2 and Comparative Example 1 as an exemplary embodiment of the present application.

FIG. 9 is a set of views illustrating the selectivity for ethylene according to the conversion of acetylene during a hydrogenation reaction using the catalysts according to Examples 3 to 5 as an exemplary embodiment of the present application.

FIG. 10 is a view illustrating the results of evaluating the long-term stability of the catalysts according to Example 1 and Comparative Example 1 as an exemplary embodiment of the present application.

DETAILED DESCRIPTION

Hereinafter, the present specification will be described in more detail.

When one member is disposed "on" another member in the present specification, this comprises not only a case where the one member is brought into contact with another member, but also a case where still another member is present between the two members.

When one part "comprises" one constituent element in the present specification, unless otherwise specifically described, this does not mean that another constituent element is excluded, but means that another constituent element may be further comprised.

As described above, it is common to use a catalyst in which Pd is supported on an alumina support as a catalyst for a hydrogenation reaction in the related art. However, the catalyst as described above has a problem in that the catalyst replacement cycle is short due to the rapid deactivation of the catalyst, and thus has a problem in that the process cost may be increased. Further, in order to improve the selectivity for the product of hydrogenation reaction in the related art, a modifier was introduced, but the introduction of the modifier has a problem in that the process cost may be increased and an additional separation process is required.

In a hydrogenation reaction of acetylene for removing a trace amount of acetylene comprised in an ethylene raw material, since a large amount of ethylene is present together with acetylene, ethylene is consumed together in a process of removing acetylene. In addition, in the hydrogenation reaction of acetylene, coke is rapidly formed on a catalyst, so the deactivation of the catalyst may occur in a short time.

Thus, the present application was intended to develop a catalyst for a hydrogenation reaction, which has excellent selectivity for the product of hydrogenation reaction and excellent long-term stability of the catalyst. In particular, the present inventors have conducted research in which a polymer containing sulfur is additionally supported on a catalyst for a hydrogenation reaction in which a catalytic component is supported on a porous carrier, thereby completing the present application.

The catalyst for a hydrogenation reaction according to an exemplary embodiment of the present application comprises: a porous carrier; a catalytic component supported on the porous carrier; and a polymer provided on at least a part of the surfaces of the porous carrier and the catalytic component and comprising a repeating unit represented by the following Chemical Formula 1.

[Chemical Formula 1]

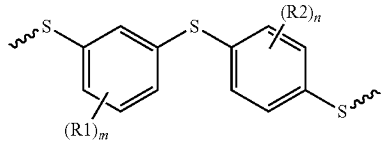

In Chemical Formula 1,

R1 and R2 are the same as or different from each other, and are each independently hydrogen, an alkyl group having 1 to 10 carbon atoms, or an aryl group having 6 to 20 carbon atoms, or adjacent groups of R1 or R2 may be bonded to each other to form a hydrocarbon ring, and m and n are each independently an integer from 0 to 4.

In an exemplary embodiment of the present application, in the chemical formula means a point where the repeating unit is linked.

In an exemplary embodiment of the present application, Chemical Formula 1 may be represented by any one of the following Chemical Formulae 2 to 6.

[Chemical Formula 2]

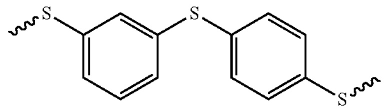

[Chemical Formula 3]

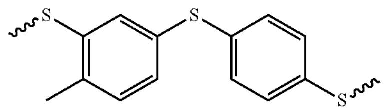

[Chemical Formula 4]

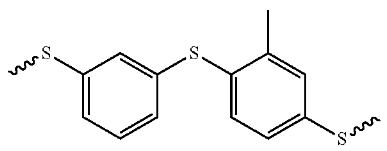

[Chemical Formula 5]

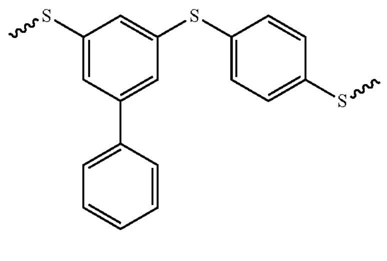

-continued

[Chemical Formula 6]

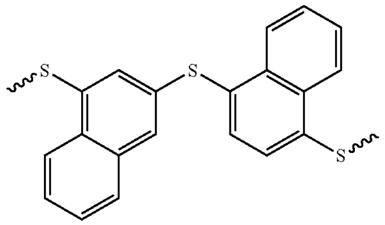

In an exemplary embodiment of the present application, the alkyl group of Chemical Formula 1 may be straight-chained or branched, and the number of carbon atoms thereof is preferably 1 to 10. Specific examples of the alkyl group comprise a methyl group, an ethyl group, a propyl group, an isopropyl group, a butyl group, an n-butyl group, an isobutyl group, a tert-butyl group, a sec-butyl group, a 1-methylbutyl group, a 1-ethylbutyl group, and the like, but are not limited thereto.

In an exemplary embodiment of the present application, specific examples of the aryl groups of Chemical Formula 1 may comprise a phenyl group, a biphenyl group, a terphenyl group, a quaterphenyl group, a naphthyl group, an anthracenyl group, a phenanthrenyl group, a pyrenyl group, and the like, but are not limited thereto.

In an exemplary embodiment of the present application, both R1 and R2 of Chemical Formula 1 may be hydrogen.

In an exemplary embodiment of the present application, the polymer comprising the repeating unit represented by Chemical Formula 1 is a polymer comprising a polyphenylene sulfide structure in which a meta-phenylene bond and a para-phenylene bond are hybridized. The polymer containing the repeating unit represented by Chemical Formula 1 has excellent solubility in an organic solvent, has a structure close to amorphous, and has a feature of high thermal stability. Furthermore, the polymer represented by the Chemical Formula 1 is characterized in that the activity and long-term stability of the catalyst for a hydrogenation reaction can be more effectively improved even with a small content.

In an exemplary embodiment of the present application, the polymer comprising the repeating unit represented by Chemical Formula 1 may be provided on at least a part of the surfaces of the porous carrier and the catalytic component. Further, the polymer comprising the repeating unit represented by Chemical Formula 1 may be provided on the entire surfaces of the porous carrier and the catalytic component to form a polymer layer.

In the hydrogenation reaction of alkyne to alkene, in the case of an alumina- or silica-based metal supported catalyst in the related art, both alkyne and alkene are easily adsorbed on the surface of the metal, so that hydrogenation of alkyne to alkene and hydrogenation of alkene to alkane are non-selectively accomplished. However, as in an exemplary embodiment of the present application, when the polymer comprising the repeating unit represented by Chemical Formula 1 is additionally comprised, the surface of an active metal is surrounded by the polymer due to the strong binding power between the polymer and the active metal. Therefore, based on the active metal, a reactant exhibiting a relatively stronger binding power than the binding power between the active metal and the polymer, such as alkyne, is adsorbed on the active metal, but reactants exhibiting a relatively weaker binding power, such as alkene, have a reaction characteristic that the reactants cannot be adsorbed on the active metal. Due to these characteristics, a catalyst in which a polymer comprising the repeating unit represented by Chemical Formula 1 is additionally supported on a porous carrier on which an active metal is supported can show high selectivity in a hydrogenation reaction of alkyne to alkene by suppressing the hydrogenation reactivity of alkene while maintaining the hydrogenation reactivity of alkyne as it is.

In an exemplary embodiment of the present application, the polymer comprising the repeating unit represented by Chemical Formula 1 may have a weight average molecular weight of 1,000 g/mol to 10,000 g/mol, and 1,500 g/mol to 7,000 g/mol. When the polymer comprising the repeating unit represented by Chemical Formula 1 has a weight average molecular weight of less than 1,000 g/mol, the catalytic stability becomes low, so that it is not preferred because the deactivation of the catalyst due to polymer loss may occur during the hydrogenation reaction. In addition, when the polymer comprising the repeating unit represented by Chemical Formula 1 has a weight average molecular weight of more than 10,000 g/mol, it is not preferred because the solubility may be lowered and the amount of polymer required to modify the surface of the active metal may be increased.

The weight average molecular weight is one of the average molecular weights in which the molecular weight is not uniform and the molecular weight of any polymer material is used as a reference, and is a value obtained by averaging the molecular weight of a component molecular species of a polymer compound having a molecular weight distribution by a weight fraction. The weight average molecular weight may be measured by a gel permeation chromatography (GPC) method.

In an exemplary embodiment of the present application, as the porous carrier, those known in the art may be used, and are not particularly limited. For example, the porous carrier may comprise one or more of silica, alumina, magnesia, silica-alumina, silica-magnesia and alumina-magnesia, and is preferably alumina, but is not limited thereto.

In an exemplary embodiment of the present application, the catalytic component may comprise one or more of platinum (Pt), palladium (Pd), ruthenium (Ru), iron (Fe), nickel (Ni), cobalt (Co), molybdenum (Mo), gold (Au), silver (Ag), copper (Cu), titanium (Ti), gallium (Ga), cerium (Ce), aluminum (Al), zinc (Zn), and lanthanum (La).

In an exemplary embodiment of the present application, a content of the catalytic component may be 0.01 wt % to 10 wt % and 0.05 wt % to 5 wt %, based on a total weight of the catalyst for a hydrogenation reaction. When the content of the catalytic component is less than 0.01 wt % based on the total weight of the catalyst for a hydrogenation reaction, the reactivity of the catalyst may deteriorate, so that the content is not preferred. Further, when the content of the catalytic component is more than 10 wt %, a relatively large amount of active metal is contained compared to the porous support, so that the active metal may not be easily bonded to the porous carrier, and accordingly, the selectivity of alkene is lowered by hydrogenation reaction, so that the actual benefit of the hydrogenation reaction caused by the increase in weight may be decreased.

In an exemplary embodiment of the present application, a content of the polymer may be 0.01 wt % to 5 wt % and 0.05 wt % to 2 wt %, based on a total weight of the catalyst for a hydrogenation reaction. When the content of the catalyst is less than 0.01 wt % based on the total weight of the catalyst for a hydrogenation reaction, the effect of enhancing the selectivity for the reactant and the catalyst stability is insignificant, so that the content is not preferred. In addition, when the content of the polymer exceeds 5 wt %, the catalytic activity may be significantly reduced, so that the content is not preferred.

The method for producing a catalyst for a hydrogenation reaction according to an exemplary embodiment of the present application comprises: supporting a catalytic component on a porous carrier; and supporting a polymer comprising the repeating unit represented by Chemical Formula 1 on the porous carrier on which the catalytic component is supported.

In the method for producing a catalyst for a hydrogenation reaction according to an exemplary embodiment of the present application, contents on the porous carrier, the catalytic component, the polymer comprising the repeating unit represented by Chemical Formula 1, and the like are the same as those described above.

In an exemplary embodiment of the present application, the supporting of the catalytic component on the porous carrier may use a method known in the art and is not particularly limited. For example, in the method for supporting a catalytic component on a polymer support, after an aqueous solution or organic solution (supporting solution) containing a compound as a precursor for the catalytic component is prepared, a catalyst may be synthesized by using an immersion method in which the polymer support is immersed in the supporting solution, dried, and then reduced with hydrogen gas and the catalytic component is supported, or by stirring the resulting polymer support with metal nanoparticles reduced in advance. As a precursor for the catalytic component, an organic metal compound such as $Pd(acac)_2$, $Pd(NH_3)_4(NO_3)_2$, $Pd(NO_3)_2$, $Pt(acac)_2$, and $Pt(NO_3)_2 \cdot 4NH_3$ may be used, but the precursor is not limited thereto.

In an exemplary embodiment of the present application, the method for producing a polymer comprising the repeating unit represented by Chemical Formula 1 is specifically described in exemplary embodiments to be described below. For example, the polymer comprising the repeating unit represented by Chemical Formula 1 may be synthesized by condensation polymerization of a metal sulfide, an organic monomer comprising a meta-bond, and an organic monomer comprising a para-bond. In particular, since a solid obtained after the condensation polymerization is obtained with an organic monomer that cannot participate in the polymer polymerization reaction and some sulfur compounds mixed with the polymer, in an exemplary embodiment of the present application, impurities were effectively removed by introducing a purification process as in the exemplary embodiments to be described below.

In an exemplary embodiment of the present application, the supporting of the polymer comprising the repeating unit represented by Chemical Formula 1 on the porous carrier on which the catalytic component is supported may use an immersion method in which after an organic solution (supporting solution) containing the polymer is prepared and the porous carrier on which the catalytic component is supported is immersed in the supporting solution, and then dried, the porous carrier is subjected to reduction process with hydrogen gas, and the catalytic component is supported.

As an exemplary embodiment of the present application, the method for producing a catalyst for a hydrogenation reaction is schematically illustrated in the following FIG. 1.

The catalyst according to an exemplary embodiment of the present application may be applied to a hydrogenation reaction. For example, the catalyst may be applied to a hydrogenation reaction of alkene from alkyne. The catalyst according to an exemplary embodiment of the present application may be applied equally not only to acetylene, but also to a hydrocarbon compound having a triple bond. Examples of the hydrocarbon compound comprise propyne, butyne, pentyne, hexayne, heptyne, octyne, and the like. Furthermore, in a compound comprising a functional group other than the triple bond or a double bond, for example, a compound having a benzene ring such as phenylacetylene, an alkyne compound having a carbonyl group, an alkyne compound having a carbonyl group, an alkyne compound having an alcohol group, an alkyne compound having an amine group, and the like, a hydrogenolysis reaction is suppressed, and only an alkyne group may be applied to a selective hydrogenation reaction to an alkene group.

MODE FOR INVENTION

Hereinafter, the present application will be described in detail with reference to Examples for specifically describing the present application. However, the Examples according to the present application may be modified in various forms, and it is not interpreted that the scope of the present application is limited to the Examples described in detail below. The Examples of the present application are provided for more completely explaining the present application to the person with ordinary skill in the art.

EXAMPLES

<Synthesis Example 1> Synthesis of Polymer Comprising Repeating Unit Represented by Chemical Formula 2

After 16.8 g of sodium sulfide hydrate (61.3 wt % $Na_2S$) and 70 g of n-methyl-2-pyrrolidone (NMP) were mixed, the resulting mixture was heated to 473 K and dehydrated, and then the mixture was cooled to 373 K. A solution in which 7.35 g of m-dichlorobenzene, 7.35 g of p-dichlorobenzene and 15 g of NMP were mixed was injected into the mixture, pressure was increased up to 6 bar using argon gas, and then a polymer was polymerized under stirring at 503 K for 24 hours.

After polymerization, since the obtained solid is obtained with organic monomers that could not participate in the polymer polymerization reaction and some elemental sulfur compounds mixed with the polymer, impurities were effectively removed by introducing the purification process presented below.

As a result of the synthesis, organic impurities and NMP were removed by mixing the obtained solution with 340 g of methanol, and a solid was obtained by removing only the supernatant through a centrifuge.

The obtained solid was mixed with 200 g of a 0.5 M NaOH aqueous solution, the resulting solution was stirred at 333 K for 12 hours to remove trace amounts of elemental sulfur components present in the solid, and the resulting product was washed with distilled water. Thereafter, the product was dried at 323 K for 24 hours, and the produced polymer was denoted as "m, p-PPS".

<Synthesis Example 2> Synthesis of Polymer Comprising Repeating Unit Represented by Chemical Formula 3

After 16.8 g of sodium sulfide hydrate (61.3 wt % $Na_2S$) and 70 g of n-methyl-2-pyrrolidone (NMP) were mixed, the resulting mixture was heated to 473 K and dehydrated, and then the mixture was cooled to 373 K. A solution in which 8.05 g of 2,4-dichlorotoluene, 7.35 g of p-dichlorobenzene and 15 g of NMP were mixed was injected into the mixture, pressure was increased up to 6 bar using argon gas, and then a polymer was polymerized under stirring at 503 K for 24 hours.

After polymerization, since the obtained solid is obtained with organic monomers that could not participate in the polymer polymerization reaction and some elemental sulfur compounds mixed with the polymer, impurities were effectively removed by introducing the purification process presented below.

As a result of the synthesis, organic impurities and NMP were removed by mixing the obtained solution with 340 g of methanol, and a solid was obtained by removing only the supernatant through a centrifuge.

The obtained solid was mixed with 200 g of a 0.5 M NaOH aqueous solution, the resulting solution was stirred at 333 K for 12 hours to remove trace amounts of elemental sulfur components present in the solid, and the resulting product was washed with distilled water. Thereafter, the product was dried at 323 K for 24 hours, and the produced polymer is represented by "m(t), p-PPS".

<Synthesis Example 3> Synthesis of Polymer Comprising Repeating Unit Represented by Chemical Formula 4

After 16.8 g of sodium sulfide hydrate (61.3 wt % $Na_2S$) and 70 g of n-methyl-2-pyrrolidone (NMP) were mixed, the resulting mixture was heated to 473 K and dehydrated, and then the mixture was cooled to 373 K. A solution in which 7.35 g of m-dichlorobenzene, 8.05 g of 2,5-dichlorotoluene and 15 g of NMP were mixed was injected into the mixture, pressure was increased up to 6 bar using argon gas, and then a polymer was polymerized under stirring at 503 K for 24 hours.

After polymerization, since the obtained solid is obtained with organic monomers that could not participate in the polymer polymerization reaction and some elemental sulfur compounds mixed with the polymer, impurities were effectively removed by introducing the purification process presented below.

As a result of the synthesis, organic impurities and NMP were removed by mixing the obtained solution with 340 g of methanol, and a solid was obtained by removing only the supernatant through a centrifuge.

The obtained solid was mixed with 200 g of a 0.5 M NaOH aqueous solution, the resulting solution was stirred at 333 K for 12 hours to remove trace amounts of elemental sulfur components present in the solid, and the resulting product was washed with distilled water. Thereafter, the product was dried at 323 K for 24 hours, and the produced polymer was denoted as "m, p(t)-PPS".

<Synthesis Example 4> Synthesis of Polymer Comprising Repeating Unit Represented by Chemical Formula 5

After 16.8 g of sodium sulfide hydrate (61.3 wt % $Na_2S$) and 70 g of n-methyl-2-pyrrolidone (NMP) were mixed, the resulting mixture was heated to 473 K and dehydrated, and then the mixture was cooled to 373 K. A solution in which 11.2 g of 3,5-dichloro-1,1'-biphenyl, 7.35 g of p-dichlorobenzene and 15 g of NMP were mixed was injected into the mixture, pressure was increased up to 6 bar using argon gas, and then a polymer was polymerized under stirring at 503 K for 24 hours.

After polymerization, since the obtained solid is obtained with organic monomers that could not participate in the polymer polymerization reaction and some elemental sulfur compounds mixed with the polymer, impurities were effectively removed by introducing the purification process presented below.

As a result of the synthesis, organic impurities and NMP were removed by mixing the obtained solution with 340 g of methanol, and a solid was obtained by removing only the supernatant through a centrifuge.

The obtained solid was mixed with 200 g of a 0.5 M NaOH aqueous solution, the resulting solution was stirred at 333 K for 12 hours to remove trace amounts of elemental sulfur components present in the solid, and the resulting product was washed with distilled water. Thereafter, the product was dried at 323 K for 24 hours, and the produced polymer is represented by "m(bp), p-PPS".

<Experimental Example 1> Structural and Physicochemical Property Analysis of Synthesized Polymers In order to confirm the constituent components of the polymers produced in Synthesis Examples 1 to 4, elemental analysis and a $^{13}C$ NMR analysis were performed, and then the results are shown in Table 1 and FIG. 2.

As shown in the results in the following Table 1, the polymer produced in Synthesis Example 1 had similar constituent components as commercially available p-PPS (182354, Sigma-Aldrich). Further, the polymers produced in Synthesis Examples 1 to 4 had a C/S ratio similar to the theoretically calculated value. As in the results in the following FIG. 2, it was understood that the polymers produced in Synthesis Examples 1 to 4 were present to have structures comprising the repeating units represented by Chemical Formulae 2 to 5, respectively.

TABLE 1

| | C (wt %) | S (wt %) | C/S (mol/mol) | C/S (theoretical value) (mol/mol) |
|---|---|---|---|---|
| p-PPS | 66.90 | 29.13 | 6.09 | 6.00 |
| m, p-PPS | 66.99 | 28.76 | 6.11 | 6.00 |
| m(t), p-PPS | 68.46 | 28.31 | 6.47 | 6.50 |
| m, p(t)-PPS | 69.33 | 28.58 | 6.45 | 6.50 |
| m(bp), p-PPS | 72.58 | 21.70 | 8.92 | 9.00 |

In addition, as an exemplary embodiment of the present application, the results of evaluating the solubility characteristics of the polymers according to Synthesis Examples 1 to 4 are illustrated in the following FIG. 3. More specifically, to observe the solubility the polymers produced in Synthesis Examples 1 to 4 in tetrahydrofuran (THF), the results of dissolving the polymer in tetrahydrofuran at 1:500 are illustrated in the following FIG. 3. As a result, it can be confirmed that the polymers produced in Synthesis Examples 1 to 4 have high solubility in THF unlike p-PPS.

Further, as an exemplary embodiment of the present application, to measure the physicochemical properties of the polymers according to Synthesis Examples 1 to 4, TGA analysis was performed under XRD analysis and He conditions, and then the results are illustrated in the following FIGS. 4 and 5, respectively. It can be confirmed that the polymers produced in Synthesis Examples 1 to 4 show low crystallinity unlike p-PPS as shown in the results of the following FIG. 4, and have high thermal stability as shown in the results of the following FIG. 5.

Comparative Example 1

After 0.28 g of a $Pd(NH_3)_4(NO_3)_2$ aqueous solution (10 wt %) was mixed with 1 g of distilled water, the resulting mixture was supported on 10 g of $\alpha$-$Al_2O_3$(Alfa-aesar) by a moisture impregnation method, and then dried at 333 K for 12 hours. After drying, the corresponding sample was fired under atmospheric conditions at 673 K for 2 hours and then subjected to reduction treatment under hydrogen conditions at 673 K. The produced catalyst is represented by "Pd/$\alpha$-$Al_2O_3$".

<Example 1> Production of 0.30PPS/Pd/$\alpha$-$Al_2O_3$

A solution prepared by mixing 0.03 g of m, p-PPS produced in Synthesis Example 1 with 10 g of THF was supported on 10 g of Pd/$\alpha$-$Al_2O_3$ of Comparative Example 1 and dried at room temperature for 12 hours. After drying, the corresponding sample was subjected to reduction treatment under hydrogen conditions at 373 K for 2 hours. The produced catalyst is represented by "0.30PPS/Pd/$\alpha$-$Al_2O_3$" ('0.30' means wt % of m, p-PPS in the produced catalyst).

<Example 2> Production of 1.0PPS/Pd/$\alpha$-$Al_2O_3$

A solution prepared by mixing 0.1 g of m, p-PPS produced in Synthesis Example 1 with 10 g of THF was supported on 10 g of Pd/$\alpha$-$Al_2O_3$ of Comparative Example 1 and dried at room temperature for 12 hours. After drying, the corresponding sample was subjected to reduction treatment under hydrogen conditions at 373 K for 2 hours. The prepared catalyst is represented by "1.0PPS/Pd/$\alpha$-$Al_2O_3$" ('1.0' means wt % of m, p-PPS in the prepared catalyst).

<Example 3> Production of 0.30 m(t), p-PPS/Pd/$\alpha$-$Al_2O_3$

A solution prepared by mixing 0.03 g of m(t), p-PPS produced in Synthesis Example 2 with 10 g of THF was supported on 10 g of Pd/$\alpha$-$Al_2O_3$ of Comparative Example 1 and dried at room temperature for 12 hours. After drying, the corresponding sample was subjected to reduction treatment under hydrogen conditions at 373 K for 2 hours. The produced catalyst is "0.30 m(t), p-PPS/Pd/$\alpha$-$Al_2O_3$" ('0.30' means wt % of m(t), p-PPS in the produced catalyst).

<Example 4> Production of 0.30 m, p(t)-PPS/Pd/$\alpha$-$Al_2O_3$

A solution prepared by mixing 0.03 g of m, p(t)-PPS produced in Synthesis Example 3 with 10 g of THF was supported on 10 g of Pd/$\alpha$-$Al_2O_3$ of Comparative Example 1 and dried at room temperature for 12 hours. After drying, the corresponding sample was subjected to reduction treatment under hydrogen conditions at 373 K for 2 hours. The produced catalyst is represented by "0.30 m, p(t)-PPS/Pd/$\alpha$-$Al_2O_3$" ('0.30' means wt % of m, p(t)-PPS in the produced catalyst).

<Example 5> Production of 0.30 m(Bp), p-PPS/Pd/$\alpha$-$Al_2O_3$

A solution prepared by mixing 0.03 g of m(bp), p-PPS produced in Synthesis Example 4 with 10 g of THF was supported on 10 g of Pd/$\alpha$-$Al_2O_3$ of Comparative Example 1 and dried at room temperature for 12 hours. After drying, the corresponding sample was subjected to reduction treatment under hydrogen conditions at 373 K for 2 hours. The produced catalyst is "0.30 m(bp), p-PPS/Pd/$\alpha$-$Al_2O_3$" ('0.30' means wt % of m(bp), p-PPS in the produced catalyst).

<Experimental Example 2> Structural and Characteristic Analysis of Catalyst for Hydrogenation Reaction In order to confirm the state of active metals of the catalysts synthesized in Example 1 and Comparative Example 1, a transmission electron microscope (TEM) analysis was performed, and the results are illustrated in the following FIG. 6.

As in the results in the following FIG. 6, it could be confirmed that the palladium particles having a diameter of about 1.3 nm were uniformly dispersed in both Pd/$\alpha$-$Al_2O_3$ of Comparative Example 1 and 0.30PPS/Pd/$\alpha$-$Al_2O_3$ of Example 1.

Further, in order to confirm the surface state of the active metal according to the polymer content of the catalyst of Example 1, hydrogen chemisorption was performed, and the results are illustrated in the following FIG. 7.

As shown in the results of the following FIG. 7, the amount of hydrogen adsorbed on the active metal decreased as the polymer content increased, and in the case of a catalyst in which a polymer of 0.15 wt % to 0.3 wt % of m, p-PPS or more, hydrogen adsorption was hardly observed. Through this, it could be confirmed that the surface of the active metal can be effectively modified even when a small amount of polymer is used.

<Experimental Example 3> Selective Hydrogenation Reaction of Acetylene Using Catalyst The activity and selectivity of the supported catalysts produced in the Examples and Comparative Examples were confirmed by the following method.

The hydrogenation reaction of acetylene was measured by injecting a mixed gas consisting of 0.6 kPa acetylene, 0.9 kPa hydrogen, 49.3 kPa ethylene, and a nitrogen substrate gas into 0.1 g of the catalyst under conditions of 373 K and 1 atmospheric pressure, and was analyzed using gas chromatography linked to a reactor for product analysis in the hydrogenation reaction. The conversion of the reactant and the selectivity of the product were calculated through the following Mathematical Equations 1 and 2.

Conversion (%)=(the number of moles of acetylene reacted)/(the number of moles of acetylene fed)×100 [Mathematical Equation 1]

Selectivity (%)=(the number of moles of product produced)/(the number of moles of acetylene reacted)×100 [Mathematical Equation 2]

The selectivity for ethylene according to the conversion of acetylene during a hydrogenation reaction using the catalysts according to Examples 1 and 2 and Comparative Example 1 is illustrated in the following FIG. 8. As illustrated in the results of the following FIG. 8, it could be confirmed that the PPS/Pd/α-$Al_2O_3$ catalysts of Examples 1 and 2 showed higher ethylene selectivity than the Pd/α-$Al_2O_3$ of Comparative Example 1.

The catalysts of Examples 3 to 5 supported a 0.30 wt % polymer to modify the catalyst, and the catalytic performance was confirmed under the conditions described above, and is illustrated in the following FIG. 9. As illustrated in the results of the following FIG. 9, the catalysts of Examples 3 to 5 also showed higher ethylene selectivity than Pd/α-$Al_2O_3$ of Comparative Example 1.

<Experimental Example 4> Long-Term Stability of Catalyst

The long-term stability of the active metals of the catalysts produced in Example 1 and Comparative Example 1 was confirmed by the following method.

The same procedure as in Experimental Example 3 was performed, except that the catalytic reaction was measured at 0.042 $g_{acetylene}\ g_{catalyst}^{-1}\ h^{-1}$ weight hourly space velocity (WHSV) for 120 hours.

The results of evaluating the long-term stability of the catalysts according to Example 1 and Comparative Example 1 are illustrated in the following FIG. 10. As illustrated in the results of the following FIG. 10, it could be confirmed that the 0.30PPS/Pd/α-$Al_2O_3$ catalyst of Example 1 had a long-term stability which is at least 2-fold than the catalyst of Comparative Example 1.

Analysis devices and analysis conditions applied in the present application are as follows.

1) Elemental Analysis

Used equipment: FLASH 2000 (Thermo Scientific)

2) Cross Polarization Magic-Angle Spinning $^{13}C$ Nuclear Magnetic Resonance (CP/MAS $^{13}C$ NMR)

Used equipment: AVANCE III HD (400 MHz) with wide bore 9.4 T magnet (Bruker)

Analysis method: 100.65 MHz, repetition delay time of 3 seconds. Chemical shifts were reported in ppm relative to tetramethyl silane (0 ppm).

3) X-Ray Diffractomer (XRD)

Used equipment: D2-Phaser (Bruker)

4) Thermogravimetric Analysis (TGA)

Used equipment: N-1000 (Scinco)

Analysis method: Measured under warming condition of 5 K $min^{-1}$ in He gas

5) Transmission Electron Microscope (TEM)

Used equipment: Titan Cubed G2 60-300 (FEI) at 200 kV

6) Hydrogen Chemisorption

Used equipment: ASAP2020 (Micromeritics)

7) Gas Chromatography (GC)

Used equipment: YL6500 (Younglin)

Analysis method: on-line GC equipped with flame ionized detector (FID), GS-GasPro (Agilent) column was used From the experimental results using the polymers comprising the repeating units represented by Chemical Formulae 2 to 5, similar effects can be obtained even when a functional group such as another alkyl group and aryl group having a similar action principle is additionally bonded to repeating units represented by Chemical Formulae 2 to 5.

Therefore, according to an exemplary embodiment of the present application, the selectivity of a product in a hydrogenation reaction can be improved by additionally supporting a polymer comprising the repeating unit represented by Chemical Formula 1 on a catalyst for a hydrogenation reaction in which a catalyst component is supported on a porous carrier.

Further, the catalyst for a hydrogenation reaction according to an exemplary embodiment of the present application has excellent long-term stability, and thus is characterized by being capable of improving the catalyst service life.

The invention claimed is:

1. A catalyst for a hydrogenation reaction, comprising:

a porous carrier;

a catalytic component supported on the porous carrier; and a polymer provided on at least a part of surfaces of the porous carrier and the catalytic component, the polymer comprising a repeating unit represented by Chemical Formula 1, wherein a content of the polymer is 0.01 wt % to 5 wt % based on a total weight of the catalyst for a hydrogenation reaction:

[Chemical Formula 1]

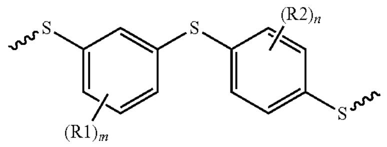

wherein, in Chemical Formula 1,

R1 and R2 are the same as or different from each other, and are each independently hydrogen, an alkyl group having 1 to 10 carbon atoms, or an aryl group having 6 to 20 carbon atoms, or adjacent groups of R1 or R2 are optionally bonded to each other to form a hydrocarbon ring, and m and n are each independently an integer from 0 to 4.

2. The catalyst of claim 1, wherein the repeating unit of Chemical Formula 1 is represented by any one of the following Chemical Formulae 2 to 6:

[Chemical Formula 2]

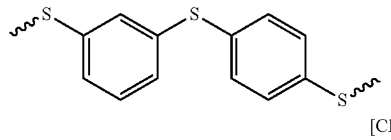

[Chemical Formula 3]

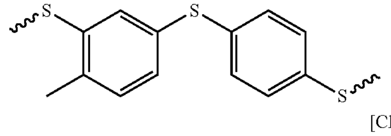

[Chemical Formula 4]

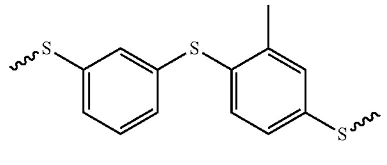

-continued

[Chemical Formula 5]

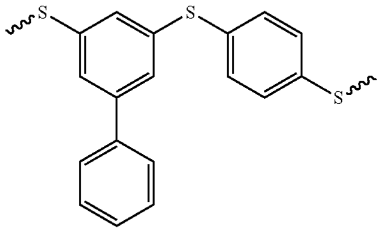

[Chemical Formula 6]

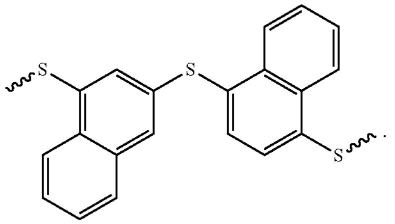

3. The catalyst of claim 1, wherein the porous carrier comprises one or more selected from the group consisting of silica, alumina, magnesia, silica-alumina, silica-magnesia and alumina-magnesia.

4. The catalyst of claim 1, wherein the catalytic component comprises one or more selected from the group consisting of platinum, palladium, ruthenium, iron, nickel, cobalt, molybdenum, gold, silver, copper, titanium, gallium, cerium, aluminum, zinc and lanthanum.

5. The catalyst of claim 1, wherein a content of the catalytic component is 0.01 wt % to 10 wt % based on a total weight of the catalyst for a hydrogenation reaction.

6. The catalyst of claim 1, wherein the catalyst for a hydrogenation reaction is a catalyst for a hydrogenation reaction of alkyne to alkene.

7. A method for producing a catalyst for a hydrogenation reaction, the method comprising:

supporting a catalytic component on a porous carrier; and supporting a polymer comprising a repeating unit represented by Chemical Formula 1 on the porous carrier on which the catalytic component is supported, wherein a content of the polymer is 0.01 wt % to 5 wt % based on a total weight of the catalyst for a hydrogenation reaction:

[Chemical Formula 1]

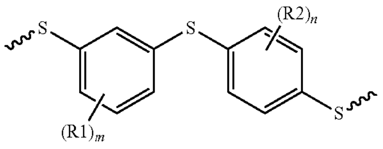

wherein, in Chemical Formula 1,

R1 and R2 are the same as or different from each other, and are each independently hydrogen, an alkyl group having 1 to 10 carbon atoms, or an aryl group having 6 to 20 carbon atoms, or adjacent groups of R1 or R2 are optionally bonded to each other to form a hydrocarbon ring, and m and n are each independently an integer from 0 to 4.

8. The method of claim 7, wherein the repeating unit of Chemical Formula 1 is represented by any one of the following Chemical Formulae 2 to 6:

[Chemical Formula 2]

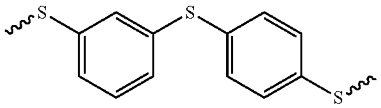

[Chemical Formula 3]

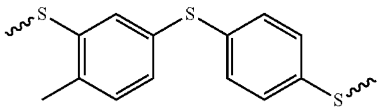

[Chemical Formula 4]

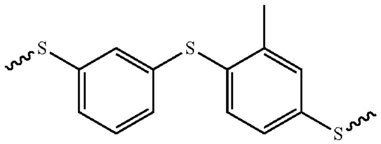

[Chemical Formula 5]

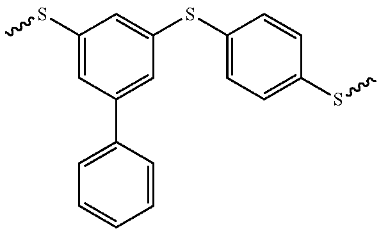

[Chemical Formula 6]

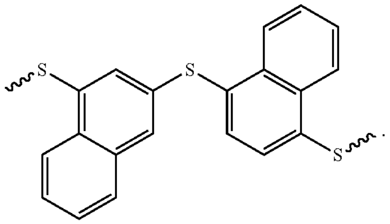

* * * * *